United States Patent [19]

Izuhara et al.

[11] Patent Number: 5,064,829

[45] Date of Patent: Nov. 12, 1991

[54] COMPOSITION OF A B VITAMIN AND MANNITOL AND A METHOD FOR PRODUCTION

[75] Inventors: Seiji Izuhara, Tondabayashi; Yoshitomi Kakiguchi, Kawanishi; Kunihiko Yokota, Suita, all of Japan

[73] Assignee: Takeda Chemical Industries, Ltd., Osaka, Japan

[21] Appl. No.: 500,249

[22] Filed: Mar. 27, 1990

[30] Foreign Application Priority Data

Mar. 29, 1989 [JP] Japan .................................. 1-79076

[51] Int. Cl.$^5$ .................. A61K 31/495; A61K 31/50; A61K 31/525; A61K 31/045
[52] U.S. Cl. .................................... 514/249; 514/251; 514/738; 514/904
[58] Field of Search ................ 514/249, 251, 738, 904

[56] References Cited

U.S. PATENT DOCUMENTS

| | | | |
|---|---|---|---|
| 4,533,542 | 8/1985 | Buddenbaum et al. | 424/497 |
| 4,605,666 | 8/1986 | Schmidt et al. | 514/474 |
| 4,684,643 | 8/1987 | Buddenbaum et al. | 514/204 |
| 4,868,180 | 9/1989 | Izuhara et al. | 514/251 |

FOREIGN PATENT DOCUMENTS 0198431 10/1986 European Pat. Off. .
WO85/01877 5/1985 PCT Int'l Appl. .

*Primary Examiner*—Richard L. Raymond
*Assistant Examiner*—Gary E. Hollinden
*Attorney, Agent, or Firm*—Wenderoth, Lind & Ponack

[57] ABSTRACT

A composition which consists of a compound belonging to the Vitamin B group and having a solubility in water at 20° C. of not more than 5%, and mannitol, is stable in itself and undergoes less influence under ambient humidity conditions.

Its good flowability is retained during storage, only with very small changes, if any.

9 Claims, No Drawings

COMPOSITION OF A B VITAMIN AND MANNITOL AND A METHOD FOR PRODUCTION

FIELD OF THE INVENTION

This invention relates to a vitamin B composition which has good stability and flowability and can advantageously be used in the food, pharmaceutical and feed industries, among others, in the manufacture of such dosage forms as powders, fine granules, capsules, pills, tablets and pellets.

BACKGROUND OF THE INVENTION

Vitamin B group compounds, such as folic acid and vitamin $B_2$, are incorporated in various food, pharmaceutical, feed and other compositions generally at low addition levels. Therefore, it is particularly required that such compounds be distributed uniformly in said compositions. In particular, the levels of addition of folic acid and vitamin $B_2$ are low in most instances. However, since they occur as fine crystalline powders having a high specific volume and showing a strong tendency toward aggregation, their flowability and handling properties are poor and unsatisfactory. Therefore, for preparing homogeneous compositions, a preliminary dilution step is generally employed in which they are diluted 10-, 100- or 1,000-fold, for instance, with starch, alpha-starch, lactose or some other appropriate excipient.

A method of obtaining free-flowing powders that has already been provided comprises contacting a composition which is spray dried with ultra-fine particle sized absorbents and effecting spray drying (Japanese Patent Application KOKAI No. 49-7415). However, the ultra-fine absorbent to be used is an inorganic material unsuited for pharmaceutical purposes. In addition, the method fails to give compositions containing folic acid or vitamin $B_2$ in high concentrations.

Another method that has been provided for preparing a vitamin $B_2$ composition capable of being directly submitted to tableting (Japanese Patent Application KOKAI No. 62-174013) gives granules on fluidized bed granulation using a macromolecular compound, such as water-soluble cellulose, as a binding agent. However, this method can hardly be applied to the manufacture of pharmaceutical preparations which should contain vitamin $B_2$ in very low concentrations, for instance.

In some of the prior art compositions, the proportion of the excipient is too high for incorporation of other active ingredients into the compositions, while in others the excipient itself is unsuited for pharmaceutical preparations. These are the problems that remain to be solved.

Accordingly, the advent of a composition which contains a vitamin B group compound, such as folic acid or vitamin $B_2$, has a low excipient content, has good flowability but no tendency toward aggregation, and can be used in the manufacture of pharmaceutical preparations is desired.

SUMMARY OF THE INVENTION

The present inventors found that a vitamin B composition which is safe, has good flowability and can be readily incorporated into various formulations can be obtained by uniformly suspending a vitamin B group compound in an aqueous solution of mannitol and subjecting the resulting suspension to spray drying.

They further found that said composition can be converted to a more stable granular powder composition by coating the same with a wax, oil or fat. The present invention has been completed based on these findings.

DETAILED DESCRIPTION OF THE INVENTION

The invention thus provides a composition which consists of a compound belonging to the vitamin B group and having a solubility in water at 20° C. of not more than 5%, and mannitol, and a method of producing such composition.

Any commercially available grade of mannitol can be used in the practice of the invention. Since mannitol is listed in the Japanese Pharmacopeia, the composition according to the invention can be used for pharmaceutical purposes.

The invention is applicable to all vitamin B group compounds which have a solubility in water at 20° C. of not more than 5%, including the following vitamin B group compounds, among others: folic acid, vitamin $B_2$, riboflavin butyrate ester, biotin, thiamine mononitrate, dibenzoylthiamine, dibenzoylthiamine hydrochloride, thiamine acetylsulfate, thiamine laurylsulfate, thiamine naphthalene-2,6-disulfonate, thiamine naphthalene-1,5-disulfonate, pyridoxine-3,4'-dioctanoate, pyridoxine-3,4'-dipalmitate, pyridoxine-3,4'-dilaurate and pyridoxine-3,4'-dilaurate hydrochloride.

The vitamin B group compounds have a solubility in water at 20° C. of not more than 5% (weight/volume), preferably not more than 3%, more preferably not more than 1%.

The vitamin B group compound content in the composition according to the invention is preferably within the range of 100 to 5,000 parts by weight, more preferably 200 to 3,000 parts by weight, more preferably 400 to 2000 parts by weight per 100 parts by weight of mannitol.

In cases where the content of the vitamin B group compound, such as folic acid or vitamin $B_2$, exceeds 5,000 parts by weight per 100 parts by weight of mannitol, the granular composition obtained may readily be disintegrated. Where the vitamin B group compound content is below 100 parts by weight per 100 parts by weight of mannitol, the high excipient (mannitol) content may lead to an excessively high mannitol proportion in final preparations manufactured by admixing the composition with another or other active ingredients. That large quantity of mannitol, which is voluminous, may cause troubles in preparing such compositions as tablets.

The composition according to the invention can be produced, for example, in the following manner.

An aqueous solution of mannitol is prepared by dissolving mannitol in distilled water. A vitamin B group compound is added to this solution and uniformly dispersed therein by means of a homomixer. The resulting suspension is then subjected to spray drying using a spray drier. Since the vitamin B group compound to be used in the practice of the invention has a solubility in water of not more than 5%, said compound remains in a suspended state in the aqueous solution of mannitol.

The aqueous solution of mannitol to be used should have a mannitol concentration of not less than 0.2% (weight/volume), preferably not less than 1%. Said concentration should appropriately be selected depending on such factors as the kind and amount of the vitamin B group compound to be contained in the composition to be prepared.

The composition obtained by spray drying generally occurs as a powder which is considerably uniform in composition. The drying is preferably performed at a drying temperature within the range of about 100°–180° C., more preferably 130°–160° C. The spray drier preferably has a disk which is rotated at a rate within the range of about 1,000–30,000 rpm (revolutions per minute), more preferably 5,000–20,000 rpm.

The powdery composition according to the invention may be coated with wax, oil or fat, which is used in an amount within the range of 0.1 to 50% by weight, preferably 5 to 30% by weight, based on said composition.

As examples of the wax, fat or oil which are usable in the practice of the invention, there may be mentioned carnauba wax, paraffins, stearic acid, white beeswax, macrogols, glycerol fatty acid esters, and various hardened fats and oils (cottonseed oil, soybean oil, palm oil, corn oil, sunflower oil, rapeseed oil, lard, beef tallow, etc.), among others.

While it is a primary object of the invention to provide a composition which comprises a single vitamin B group compound and mannitol, the invention can also provide, in another aspect thereof, a composition which contains two or more vitamin B group compounds and mannitol.

As compared with the conventional compositions in which lactose, starch or the like is used, the composition according to the invention is stable in itself and undergoes less influence under ambient humidity conditions. Therefore, its good flowability is retained during storage, only with very small changes, if any. Furthermore, the composition coated with the wax, fat or oil exerts little influence on another or other active ingredients when it is admixed with these, whereby the stability of the resulting combination composition itself is improved as well.

Since it is sufficient to use only a small amount of mannitol as an excipient in the composition according to the invention, such operations as weighing and mixing can be rationalized in the manufacture of tablets, capsules, powders, granules, pellets and other preparations.

Furthermore, since the composition according to the invention is small and uniform in grain size, it can be used for low addition level incorporation of a vitamin B group compound or compounds. The invention is particularly effective in cases where folic acid or vitamin $B_2$ is used; there, the invention affords a composition having good handling characteristics that have never been attained in the prior art.

The following examples illustrate the invention in further detail.

The ingredient materials used all occurred as powders. The sieve mesh designations are based on the Japanese Industrial Standard definition (JIS K 6900).

EXAMPLE 1

The powder composition consisting of folic acid and mannitol

Folic acid was obtained from Takeda Chemical Industries and mannitol from Imperial Chemical Industries (I.C.I.).

Folic acid (95 g) was added to a solution of 5 g of mannitol in 200 ml of distilled water and homogeneously dispersed therein by means of a homomixer (T.K. homomixer model M, manufactured by Tokushu Kika Kogyo Comp.).

This folic acid suspension was subjected to spray drying using a mobile minor type spray drier (Ashizawa-Niro Atomizer LTD.) while the homogeneity of said suspension was maintained by stirring. The drying temperature was 150° C. and the disk was rotated at 20,000 rpm.

The thus-obtained composition occurred as a yellow powder. Particle size distribution and repose angle of the composition are shown below.

| (1) Particle size distribution | |
| --- | --- |
| Particle size | Proportion |
| Plus 100-mesh sieve | 7.9% |
| Minus 330-mesh sieve | 3.9% |

(2) Repose angle: 42°.

EXAMPLE 2

The powder composition consisting of vitamin $B_2$ and mannitol

Vitamin $B_2$ was obtained from Hoffmann-La Roche Inc. and mannitol from I.C.I.

Vitamin $B_2$ (90 g) was added to a solution of 10 g of mannitol in 200 ml of distilled water and homogeneously dispersed therein by means of a homomixer (T.K. homomixer model M, manufactured by Tokushu Kika Kogyo Comp.).

This vitamin $B_2$ suspension was subjected to spray drying using a mobile minor type spray drier (Ashizawa-Niro Atomizer LTD.) while the homogeneity of the suspension was maintained by stirring. The drying temperature was 150° C. and the disk was rotated at 20,000 rpm.

The thus-obtained composition occurred as a yellow powder. Particle size distribution and repose angle of the composition are shown below.

| (1) Particle size distribution | |
| --- | --- |
| Particle size | Proportion |
| Plus 100-mesh sieve | 2.3% |
| Minus 330-mesh sieve | 5.7% |

(2) Repose angle: 40°.

EXAMPLE 3

Wax-coated powder composition consisting of folic acid and mannitol

The powdery composition consisting of folic acid and mannitol obtained in Example 1 was wax-coated by the hot hexane method. Carnauba wax was used as the wax.

Thus, in a tightly closable container, 0.5 g of carnauba wax was dissolved in 100 ml of hexane warmed to about 75° C., and 10 g of the powder composition was added to the solution with stirring by means of a stirrer. The resultant mixture was then allowed to cool to room temperature with the container tightly closed. Thereafter the mixture was filtered through a filter paper. The residue on the filter paper was dried at 40° C. under vacuum to give a wax-coated powder composition consisting of folic acid and mannitol.

EXAMPLE 4

The powder composition consisting of folic acid and mannitol

Folic acid was obtained from Takeda Chemical Industries and mannitol from I.C.I.

Folic acid (90 g) was added to a solution of 10 g mannitol in 200 ml of distilled water and homogeneously dispersed therein with a homomixer (T.K. homomixer model M, manufactured by Tokushu Kika Kogyo Comp.).

This folic acid suspension was subjected to spray drying using a mobile minor type spray drier (Ashizawa-Niro Atomizer LTD.) while homogeneity of the suspension was maintained by stirring. The drying temperature was 50° C. and the disk was rotated at 20,000 rpm. The thus-obtained dry composition occurred as a yellow powder. Particle size distribution and repose angle of the composition are shown below.

| (1) Particle size distribution | |
| --- | --- |
| Particle size | Proportion |
| Plus 100-mesh sieve | 8.1% |
| Minus 330-mesh sieve | 3.3% |

(2) Repose angle: 41°.

EXAMPLE 5

The powder composition consisting of vitamin $B_2$ and mannitol

Vitamin $B_2$ was obtained from Hoffmann-La Roche Inc. and mannitol from I.C.I.

Vitamin $B_2$ (97 g) was added to a solution of 3 g of mannitol in 200 ml of distilled water and homogeneously dispersed therein by means of a homomixer (T.K. homomixer model M, manufactured by Tokushu Kika Kogyo Comp.).

This vitamin $B_2$ suspension was subjected to spray drying using a mobile minor type spray drier (Ashizawa-Niro Atomizer LTD.) while the homogeneity of the suspension was maintained by stirring. The drying temperature was 150° C. and the disk was rotated at 20,000 rpm.

The thus-obtained composition occurred as a yellow powder. Particle size distribution and repose angle of the composition are shown below.

| (1) Particle size distribution | |
| --- | --- |
| Particle size | Proportion |
| Plus 100-mesh sieve | 1.0% |
| Minus 330-mesh sieve | 10.7% |

Repose angle: 42.2°.

TEST METHOD 1

Folic acid assay

In the experimental examples, the folic acid assay procedure was performed using light-impermeable containers and avoiding direct sunlight. Assay preparations were prepared by extracting 50 mg of a sample with 20 ml of a dichloromethane-1N aqueous ammonia mixture (1:1) and subjected to assay by the USP (U.S. Pharmacopeia) method (high-performance liquid chromatography).

TEST METHOD 2

Vitamin $B_2$ assay

In the experimental examples, the vitamin $B_2$ assay procedure was performed using light-impermeable containers and avoiding direct sunlight. Assay preparations were prepared by extracting 30 mg of a sample with 50 ml of 5N acetic acid and subjected to assay by the USP method (colorimetry).

TEST METHOD 3

Flowability evaluation (measurement of repose angle)

In the experimental examples, the compositions containing folic acid or vitamin $B_2$ were evaluated for their flowability as follows: Fifty-five-gram portions of each sample composition were placed in amber-glass desiccators respectively conditioned to 11%, 20%, 31%, 43%, 53%, 68%, 75%, 82% and 91% and, after 2 weeks of storing at 40° C., repose angle measurements were performed using a Konishi model FK repose angle measuring apparatus (Konishi Medical & Surgical Co.).

EXPERIMENTAL EXAMPLE 1

Stability and repose angle data for a folic acid composition and a vitamin $B_2$ composition

| | (After 2 weeks of storage at 40° C.) | | | |
| --- | --- | --- | --- | --- |
| Storage condition | Folic acid composition | | Vitamin $B_2$ composition | |
| (Relative humidity) | Content | Repose angle | Content | Repose angle |
| Initial | 100% | 41° | 100% | 40° |
| 11 | 100 | 40 | 99.8 | 42 |
| 20 | 99.5 | 40 | 100 | 40 |
| 31 | 99.7 | 41 | 100 | 40 |
| 43 | 99.5 | 41 | 99.9 | 40 |
| 53 | 99.3 | 40 | 99.7 | 41 |
| 68 | 99.5 | 41 | 100 | 42 |
| 75 | 99.2 | 41 | 99.7 | 40 |
| 82 | 99 | 42 | 100 | 41 |
| 91 | 98.5 | 42 | 100 | 40 |

Contents: Expressed in terms of residual percentage.

As is evident from the data given in the above table, the folic acid composition and vitamin $B_2$ composition obtained in Example 1 and Example 2, respectively, did not suffer any substantial flowability losses during 2 weeks of storage at 40° C. under various humidity conditions ranging from the highest 91% relative humidity to the lowest 11% relative humidity. The compositions retained their respective active ingredient contents stably.

EXPERIMENTAL EXAMPLE 2

Stability of folic acid in a premix

The wax-coated composition obtained in Example 3 was packed in the form of a premix into a glass bottle and stored airtight therein under the conditions specified in the table given below, followed by folic acid assay and residual percentage calculation.

| Folic acid residual percentage | | |
| --- | --- | --- |
| Storage conditions | Composition of Example 3 | Folic acid bulk substance |
| 40° C., 1 month | 98% | 70% |

As the data in the above table indicate, the wax-coated folic acid composition obtained by the method of the invention was more stable than the folic acid bulk substance used as a control.

The premix used was prepared according to the following formula (folic acid content=100 mg/kg of premix)

| Ingredient | Content (per kg) |
| --- | --- |
| Vitamin A | 1,250,000 IU |
| Vitamin D | 125,000 IU |
| dl-α-tocopheryl acetate | 7.5 g |
| Phytonadione | 0.013 g |
| Vitamin $B_1$ | 0.5 g |
| Vitamin $B_2$ | 0.45 g |
| Vitamin $B_6$ | 0.5 g |
| Vitamin $B_{12}$ | 0.01 g |
| Biotin | 0.001 g |
| Calcium D-pantothenate | 3.0 g |
| Nicotainamide | 5.0 g |
| Choline chloride | 5.0 g |
| Manganese (manganese carbonate) | 1.0 g |
| Iron (iron sulfate) | 4.5 g |
| Calcium phosphate | 30.0 g |
| Copper (dried copper sulfate) | 0.5 g |
| Zinc (zinc carbonate) | 3.75 g |
| Iodine (calcium iodate) | 0.0375 g |
| Others (lactose, corn starch, etc.) | Quantity sufficient to make the whole quantity 1 kg |

EXPERIMENTAL EXAMPLE 3

Flowability of a folic acid composition and of a vitamin $B_2$ composition

The folic acid composition obtained in Example 4 and the vitamin $B_2$ composition obtained in Example 2 as well as folic acid compositions and vitamin $B_2$ compositions containing the conventional excipient lactose or corn starch were subjected to flowability and stability testing for investigating possible influences of the humidity during storage on the flowability and stability of each composition.

Each composition was allowed to stand at 40° C. for 2 weeks under the respective humidity conditions (11% to 91% relative humidity) specified in the two tables given below, followed by water content determinations and repose angle measurements.

The compositions used for comparison were as follows:

| (Folic acid) | |
| --- | --- |
| 10% Lactose: | |
| Lactose | 10 g |
| Folic acid | 90 g |
| 10% Corn starch: | |
| Corn starch | 10 g |
| Folic acid | 90 g |
| (Vitamin $B_2$) | |
| 10% Lactose: | |
| Lactose | 10 g |
| Vitamin $B_2$ | 90 g |
| 10% Corn starch: | |
| Corn starch | 10 g |
| Vitamin $B_2$ | 90 g |

The above compositions for comparison were prepared by the same spray drying method as used in Examples 1 to 3 and submitted to measurements.

A 2-gram portion of the samples containing folic acid stored at a temperature of 40° C. for 2 weeks under the specified humidity conditions (11% to 91% relative humidity) was assayed for water content by the Karl-Fischer method and the increase or decrease in water content was calculated relative to the initial value.

A 0.5-gram portion of the samples containing vitamin $B_2$ stored at a temperature of 40° C. for 2 weeks under the specified humidity conditions (11% to 91% relative humidity) was heated at a temperature of 105° for 2 to 3 hours, and the increase or decrease in water content was calculated relative to the initial value.

The repose angle measurement was performed with a 100-gram portion each of the samples stored at a temperature of 40° C. for 2 weeks under the specified humidity conditions (11% to 91% relative humidity) using a Konishi model FK angle-of-repose measuring apparatus (Konishi Medical & Surgical Co.). The samples were further evaluated for their flowability by eye. The measurement and evaluation results were expressed in terms of (+),(−) and (±).

| | Influences of humidity during storage (folic acid composition) | | |
| --- | --- | --- | --- |
| Relative humidity during storage (%) | 10% Lactose | 10% Corn starch | 10% Mannitol |
| 91 | + (0.96%) | + (0.54%) | + (0.66%) |
| 82 | + (0.69%) | ± (0.46%) | ± (0.50%) |
| 75 | + (0.39%) | ± (0.33%) | − (0.40%) |
| 68 | + (0.33%) | ± (0.36%) | − (0.40%) |
| 53 | + (0.17%) | ± (0.14%) | − (0.31%) |
| 43 | ± (−0.16%) | − (0.07%) | − (0.27%) |
| 31 | ± (0.44%) | − (−0.02%) | − (0.17%) |
| 20 | − (0.16%) | − (−0.10%) | − (0.07%) |
| 11 | − (0%) | − (−0.29%) | − (−0.01%) |

Repose angle: (−) for 40–45° C., (±) for 45–50°, (+) for >50°.
Each data in the parentheses (lower row): Increase or decrease in water content relative to the initial vale.

| | Influences of humidity during storage (vitamin $B_2$ composition) | | |
| --- | --- | --- | --- |
| Relative humidity during storage (%) | 10% Lactose | 10% Corn starch | 10% Mannitol |
| 91 | + (1.11%) | | + (0.13%) |
| 82 | + (0.18%) | + (1.17%) | − (0.80%) |
| 75 | + (0.11%) | ± (0.93%) | − (0.028%) |
| 68 | ± (−0.01%) | ± (0.80%) | − (0.029%) |
| 53 | ± (−0.16%) | ± (0.57%) | − (0.028%) |
| 43 | ± (−0.17%) | − (0.40%) | − (0.028%) |

-continued

| Influences of humidity during storage (vitamin B$_2$ composition) | | | |
|---|---|---|---|
| Relative humidity during storage (%) | 10% Lactose | 10% Corn starch | 10% Mannitol |
| 31 | — (0.23%) | — (0.22%) | — (0.01%) |
| 20 | — (0.08%) | — (0.01%) | — (−0.09%) |
| 11 | — (−0.13%) | — (−0.24%) | — (−0.09%) |

Repose angle: (−) for 40–45° C., (±) for 45–50°, (+) for >50°.
Each data in the parentheses (lower row): Increase or decrease in water content relative to the initial vale.

The data shown in the above two tables have revealed that the compositions according to the invention in which mannitol is used show higher stability and less flowability losses during storage as compared with the compositions in which lactose or corn starch, each a conventional excipient, is used.

What is claimed is:

1. A composition which consists of (1) a compound belonging to the vitamin B group and having a solubility in water at 20° C. of not more than 5% and (2) mannitol, wherein the content of (1) is within the range of 400 to 2,000 parts by weight per 100 parts by weight of mannitol.

2. A composition as claimed in claim 1, wherein the compound belonging to the vitamin B group has a solubility in water of not more than 3%.

3. A composition as claimed in claim 1, wherein the compound belonging to the vitamin B group has a solubility in water of not more than 1%.

4. A composition as claimed in claim 1, wherein the compound belonging to the vitamin B group and having a solubility in water of not more than 5% is folic acid or vitamin B$_2$.

5. A composition as claimed in claim 1, said composition being in the form of a powder.

6. A method of producing a composition consisting of (1) a compound belonging to the vitamin B group and (2) mannitol, wherein the content of (1) is within the range of 400 to 2,000 parts by weight per 100 parts be weight of mannitol, which comprises suspending a compound belonging to the vitamin B group and having a solubility in water at 20° C. of not more than 5%, in an aqueous solution of mannitol, and subjecting the resulting suspension to spray drying.

7. A method as claimed in claim 6, wherein the compound belonging to the vitamin B group and having a solubility in water of not more than 5% is folic acid or vitamin B$_2$.

8. A method as claimed in claim 6, wherein the aqueous solution of mannitol has a mannitol concentration of not less than 0.2% (weight/volume).

9. A method as claimed in claim 6, wherein the aqueous solution of mannitol has a mannitol concentration of not less than 1% (weight/volume).

* * * * *